(12) United States Patent
Sieracki et al.

(10) Patent No.: US 7,603,177 B2
(45) Date of Patent: *Oct. 13, 2009

(54) APPLYING FILTER INFORMATION TO IDENTIFY COMBINATIONS OF ELECTRODES

(75) Inventors: Jeffrey M. Sieracki, Silver Spring, MD (US); Richard B. North, Baltimore, MD (US)

(73) Assignee: Medtronic, Inc., Minneapolis, MN (US)

( * ) Notice: Subject to any disclaimer, the term of this patent is extended or adjusted under 35 U.S.C. 154(b) by 525 days.

This patent is subject to a terminal disclaimer.

(21) Appl. No.: 11/413,626

(22) Filed: Apr. 28, 2006

(65) Prior Publication Data

US 2008/0058899 A1 Mar. 6, 2008

Related U.S. Application Data

(63) Continuation of application No. 10/696,778, filed on Oct. 29, 2003, now Pat. No. 7,146,219.

(60) Provisional application No. 60/422,262, filed on Oct. 31, 2002, provisional application No. 60/503,217, filed on Sep. 15, 2003.

(51) Int. Cl.
*A61N 1/00* (2006.01)

(52) U.S. Cl. ........................................... 607/59

(58) Field of Classification Search ............... 607/46, 607/59, 62, 63
See application file for complete search history.

(56) References Cited

U.S. PATENT DOCUMENTS

| | | | |
|---|---|---|---|
| 5,370,672 A | 12/1994 | Fowler et al. | |
| 5,615,318 A | 3/1997 | Matsuura | |
| 5,938,690 A | 8/1999 | Law et al. | |
| 6,052,624 A | 4/2000 | Mann | |
| 6,308,102 B1 | 10/2001 | Sieracki et al. | |
| 6,609,032 B1 | 8/2003 | Woods et al. | |
| 6,654,027 B1 | 11/2003 | Hernandez | |
| 6,659,968 B1 | 12/2003 | McClure | |

(Continued)

FOREIGN PATENT DOCUMENTS

EP 0 811 395 12/1997

(Continued)

OTHER PUBLICATIONS

Fowler, K.R., "Neurological Stimulation System", Proceedings AAMI 21$^{st}$ Annual Meeting, Apr. 12-16, p. 27, 1986.

(Continued)

*Primary Examiner*—Scott M Getzow
(74) *Attorney, Agent, or Firm*—Shumaker & Sieffert, P.A.

(57) ABSTRACT

A programming device compares filter information to information that describes possible combinations of the electrodes within an electrode set implanted in a patient. The filter information describes at least one characteristic of valid, e.g., desired, electrode combinations, and in exemplary embodiments, is received from a user, e.g., a clinician, via a user interface of the programming device. The filter information can describe a number of electrodes in valid combinations, a fixed polarity for an electrode for valid combinations, or relational characteristics of the electrodes of valid combinations. The comparison process may be iterative. The programming device identifies a subset of the possible electrode combinations based on the comparison. By identifying the valid subset of electrode combinations based on the filter information, the programming device may reduce the amount of clinician and patient time required to program an implantable neurostimulator.

30 Claims, 6 Drawing Sheets

U.S. PATENT DOCUMENTS 7,015,935 B2     3/2006     Herget et al.
2002/0116036 A1     8/2002     Daignault, Jr. et al.

OTHER PUBLICATIONS

Fowler, K. R., North, R.B.: "Patient-interactive PC interface to implanted, multichannel stimulators," Proceedings of 39th Annual Conference on Engineering in Medicine and Biology, p. 380, 1986.

North, R.B., Fowler, K.R., "Computer-controlled, patient-interactive, multichannel, implanted neurological stimulators," Applied Neurophysiology, 50:39-41, 1987.

North, R.B., Nigrin, D.J., Szymanski, R.E., Fowler, K.R., "Computer-controlled, multichannel, implanted neurological stimulation system: Clinical assessment," Pain (Suppl.), 5:S83, 1990.

Fowler, K.R., North, R.B., "Computer-optimized neurological stimulation," Proc. Ann. Internat. Conf. IEEE Engineering Medicine and Biology Soc., 13:1692-1693, 1991.

Fowler, K.R., North, R.B., "Computer-optimized neurostimulation," APL Technical Digest, 12:192-197, 1991.

North, R.B., et al., "Spinal cord stimulation for chronic intractable pain: superiority of 'multi-channel' devices," Pain, V44, pp. 119-130, 1991.

North, R.B., Fowler, K.R., "Computer-controlled, patient-interactive neurological stimulation system," (Abstract) Acta Neurochir, 117:90, 1992.

North, R.B., Fowler, K.R., Nigrin, D.A., Szymanski, R.E., "Patient interactive, computer-controlled neurological stimulation system: Clinical efficacy in spinal cord stimulator adjustment," Journal of Neurosurgery, 76:967-972, 1992.

North, R.B., Fowler, K.R., Nigrin, D.A., Szymanski, R.E., Piantadosi, S., "Automated 'pain drawing' analysis by computer-controlled, patient-interactive neurological stimulation system," Pain, 50:51-57, 1992.

North, R.B., "Spinal Cord Stimulation for Chronic Intractable Pain," Electrical and Magnetic Stimulation of the Brain and Spinal Cord, pp. 289-301, 1993.

North, R.B., "The Role of Spinal Cord Stimulation in Contemporary Pain Management," APS Journal, vol. 2, No. 2, pp. 91-99, 1993.

North, R. B., Kidd, D. H., Zahurak, M., James, C. S., Long, D. M., "Spinal cord stimulation for chronic, intractable pain: Experience over two decades," Neurosurgery, 32:384-395, 1993.

North, R.B., Fowler, K.R., "Patient-interactive, microprocessor-controlled neurological stimulation system" (abstract), Stereotactic and Functional Neurosurgery, 62:309-315, 1994.

North, R. B., Levy, R. M., "Concensus conference on the neurosurgical management of pain," Neurosurgery, 34:756-761, 1994.

North, R. B., Kidd, D. H., Lee, M. S., Piantadosi, S., "A prospective, randomized study of spinal cord stimulation versus reoperation for the failed back surgery syndrom," Stereotactic and Functional Neurosurgery, 62:267-272, 1994.

North, R.B., et al., "Spinal Cord Stimulation For Chronic Pain," Functional Neurosurgery, vol. 6, No. 1, pp. 145-155, Jan. 1995.

North, R.B., Cutchis, P., "Spinal cord stimulation for chronic intractable pain," Spinal Cord Stimulation II, pp. 49-63, Darmstadt, Steinkopff, 1995.

North, R.B., McNamee, P., Wu, L., Piantadosi,S., "Artificial neural networks: Application to electrical stimulation of the human nervous system," (abstract) Stereotactic and Functional Neurosurgery, 65:161, 1995.

North, R. B., Kidd, D. H., Wimberly, R. L., Edwin, D., "Prognostic value of psychological testing in spinal cord stimulation patients: A prospective study," Neurosurgery, 39:301-311, 1996.

North, R. B., Kidd, D. H., Zahurak, M., Piantadosi, S., "Specificity of diagnostic nerve blocks: A prospective, randomized study of sciatica due to lumbosacral spine disease," Pain, 65:77-85, 1996.

North, R.B., McNamee, P., Wu,L., Piantodosi, S., "Artificial neural networks: Application to electrical stimulation of the human nervous system," Neurosurgical Focus, 2(1:1):1-5, 1997.

Alo, K. M. et al., "Computer Assisted and Patient Interactive Programming of Dual Octrode Spinal Cord Stimulation in the Treatment of Chronic Pain," Neuromodulation, vol. 1, No. 1, pp. 30-45, 1998.

North, R.B., Sieracki, J.N., Fowler, K.R., Alvarez, B., Cutchis, P.N., "Patient-interactive, microprocessor-controlled neurological stimulation system," Neuromodulation, 1(4):185-193, 1998.

Khalessi, A. A., Taylor, R. S., Brigham, D. D., North, R. B., "Automated, patient-interactive spinal cord stimulator adjustment: A cost-minimization analysis," Neurosurgery, 53:501-502, 2003.

North, R. B., Calkins, S. K., Campbell, D. S., Sieracki, J. M., Piantadosi, S. A., Daly, M. J., Dey, P. B., Barolat, G., "Automated, patient-interactive spinal cord stimulator adjustment: A randomized, controlled trial," Neurosurgery 52:572-580, 2003.

U.S. Appl. No. 10/696,501, entitled "Implantable Neurostimulator Programming with Battery Longevity Indication", filed Oct. 29, 2003, Richard B. North, Kim R. Fowler, Jeffrey M. Sieracki, David D. Brigham.

U.S. Appl. No. 10/696,781, entitled "Neurostimulation Therapy Manipulation", filed Oct. 29, 2003, Richard B. North, Jeffrey M. Sieracki.

U.S. Appl. No. 10/696,725, entitled "Failsafe Programming of Implantable Medical Devices", filed Oct. 29, 2003, Richard B. North, Jeffrey M. Sieracki.

U.S. Appl. No. 10/696,494, entitled "Distribution System for Neurostimulation Therapy Programming", filed Oct. 29, 2003, Richard B. North, Kim R. Fowler, Jeffrey M. Sieracki.

U.S. Appl. No. 10/696,491, entitled "Body Region Indication", filed Oct. 29, 2003, Richard B. North, Jeffrey M. Sieracki.

International Search Report for corresponding International Application No. PCT/US03/34170, dated Mar. 29, 2004, 4 pgs.

Written Opinion for corresponding International Application No. PCT/US03/34170, dated Oct. 5, 2004, 5 pgs.

Reply to Written Opinion for corresponding International Application No. PCT/US03/34170, dated Dec. 6, 2004, 3 pages.

International Preliminary Examination Report for corresponding International Application No. PCT/US03/34170, dated Dec. 16, 2004, 9 pages.

APPLYING FILTER INFORMATION TO IDENTIFY COMBINATIONS OF ELECTRODES

This application is a continuation of U.S. patent application Ser. No. 10/696,778, filed Oct. 29, 2003, which claims the benefit U.S. provisional application Ser. No. 60/422,262, filed, Oct. 31, 2002, and U.S. provisional application Ser. No. 60/503,217, filed Sep. 15, 2003. The entire content of each of these applications is incorporated herein by reference.

TECHNICAL FIELD

The invention relates to medical devices, and more particularly, to programming of implantable medical devices that deliver neurostimulation therapy.

BACKGROUND

Implantable medical devices are used to deliver neurostimulation therapy to patients to treat a variety of symptoms or conditions such as chronic pain, tremor, Parkinson's disease, epilepsy, incontinence, or gastroparesis. Typically, implantable medical devices deliver neurostimulation therapy in the form of electrical pulses via leads that include electrodes. To treat the above-identified symptoms or conditions, for example, the electrodes may be located proximate to the spinal cord, pelvic nerves, or stomach, or within the brain of a patient. The electrodes carried on one or more leads that are implanted within a patient may be referred to as an electrode set or array.

A clinician may select values for a number of programmable parameters in order to define the neurostimulation therapy to be delivered to a patient. For example, the clinician may select an amplitude, which may be a current or voltage amplitude, and pulse width for a stimulation waveform to be delivered to the patient, as well as a rate at which the pulses are to be delivered to the patient. The clinician may also select as parameters particular electrodes within an electrode set to be used to deliver the pulses, e.g., a combination of electrodes from the electrode set. A combination of electrodes may be defined by the polarities, e.g., positive, negative, or off (high impedance), of each of the electrodes within the electrode set. A group of parameter values may be referred to as a program in the sense that they drive the neurostimulation therapy to be delivered to the patient.

The process of selecting values for the parameters that provide adequate results can be time consuming, and, as a portion of the overall parameter selection process, the process of selecting combinations of electrodes can be particularly time-consuming and tedious. The clinician may need to test all possible combinations of electrodes within the set implanted in the patient, or a significant portion thereof, in order to identify one or more adequate combinations of electrodes. In some cases, the clinician may test combinations by manually specifying each combination to test based on intuition or some idiosyncratic methodology, and recording notes on the efficacy and side effects of each combination after delivery of stimulation via that combination. In this manner, the clinician is able to later compare and select from the tested combinations. As an example illustrating the magnitude of such a task, implantable medical devices commonly deliver spinal cord stimulation therapy (SCS) to a patient via two leads that include eight electrodes per lead and provide well over one million potential electrode combinations.

SUMMARY

In general, the invention is directed to techniques for identifying a subset of the possible combinations of electrodes within a set of electrodes used to deliver neurostimulation therapy to a patient. Filter information is compared to information that describes combinations of electrodes to determine whether the combinations are valid, e.g., are to be included in the subset. The filter information may be specified by a user, such as a clinician that programs an implantable medical device coupled to the electrode set for delivery of neurostimulation therapy.

The filter information may, for example, identify a number of electrodes for valid electrode combinations, identify a fixed polarity of one or more of the electrodes of the electrode set for valid electrode combinations, and/or identify a relational characteristic, e.g., contiguous or guarded electrode, of electrodes within a valid combination of electrodes. In some embodiments, the programming device receives information that describes the configuration of the electrode set, and generates some of the filter information based on the configuration. For example, the programming device may determine that some electrodes of the electrode set are unsuitable for combination as active electrodes because of their relative positions within the patient, e.g., the distance between the electrodes. The configuration information may include, for example, information describing the number of leads that carry the electrode set and their position within a patient, the number of electrodes per lead, the type of leads, the position of electrodes on leads, and/or the position of electrodes within the patient. In other words, configuration information may include information describing the spatial and/or geometric relationships of the electrodes within an electrode set and the leads that carry the electrodes.

The programming device may iteratively generate the information describing combinations of electrodes, and compare the generated information for each combination to the filter information. Combinations of electrodes generated by the comparison process may be sorted in an order different from which they were generated, e.g., a random order, for presentation within a list or as part of programs to test on the patient. In some embodiments, the filter information and electrode configuration information are stored within a memory of the programming device, e.g., as part of a record for the patient, as a compact description of the subset of combinations identified. At a later time, the subset can be recreated by the programming device using the filter information and the electrode configuration information.

In one embodiment, the invention is directed to a method that comprises comparing information that identifies combinations of electrodes from within a set of electrodes to filter information that relates to at least one characteristic of valid electrode combinations, and identifying a subset of the combinations of electrodes based on the comparison.

In another embodiment, the invention is directed to a computer-readable medium containing instructions. The instructions cause a programmable processor to compare information that identifies combinations of electrodes from within a set of electrodes to filter information that relates to at least one characteristic of valid electrode combinations, and identify a subset of the combinations of electrodes based on the comparison.

In another embodiment, the invention is directed to a device that comprises a user interface and a processor. The processor compares information that identifies combinations of electrodes from within a set of electrodes to filter information that relates to at least one characteristic of valid electrode combinations, and identifies a subset of the combinations of electrodes based on the comparison. The processor receives at least some of the filter information from a user via the user interface.

The invention may provide advantages. For example, by identifying a subset of the possible electrode combinations, a programming device according to the invention avoids testing all possible electrode combinations on a patient. Consequently, use of such a programming device may reduce the time required of the clinician and patient to program an implantable medical device for the provision of neurostimulation therapy to the patient.

Further, by automatically identifying the electrode combinations, the programming device may allow the clinician to avoid manually entering desired electrode combinations. A subset of electrode combinations generated by such a programming device may be more complete, e.g., may include a more complete listing of combinations that have the desired characteristics, than one generated by a clinician using an idiosyncratic method to identify electrode combinations to test. By storing filter and configuration information as a compact description of an identified subset, some embodiments of the programming device may reduce the memory requirements for storage of a treatment record for the patient.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
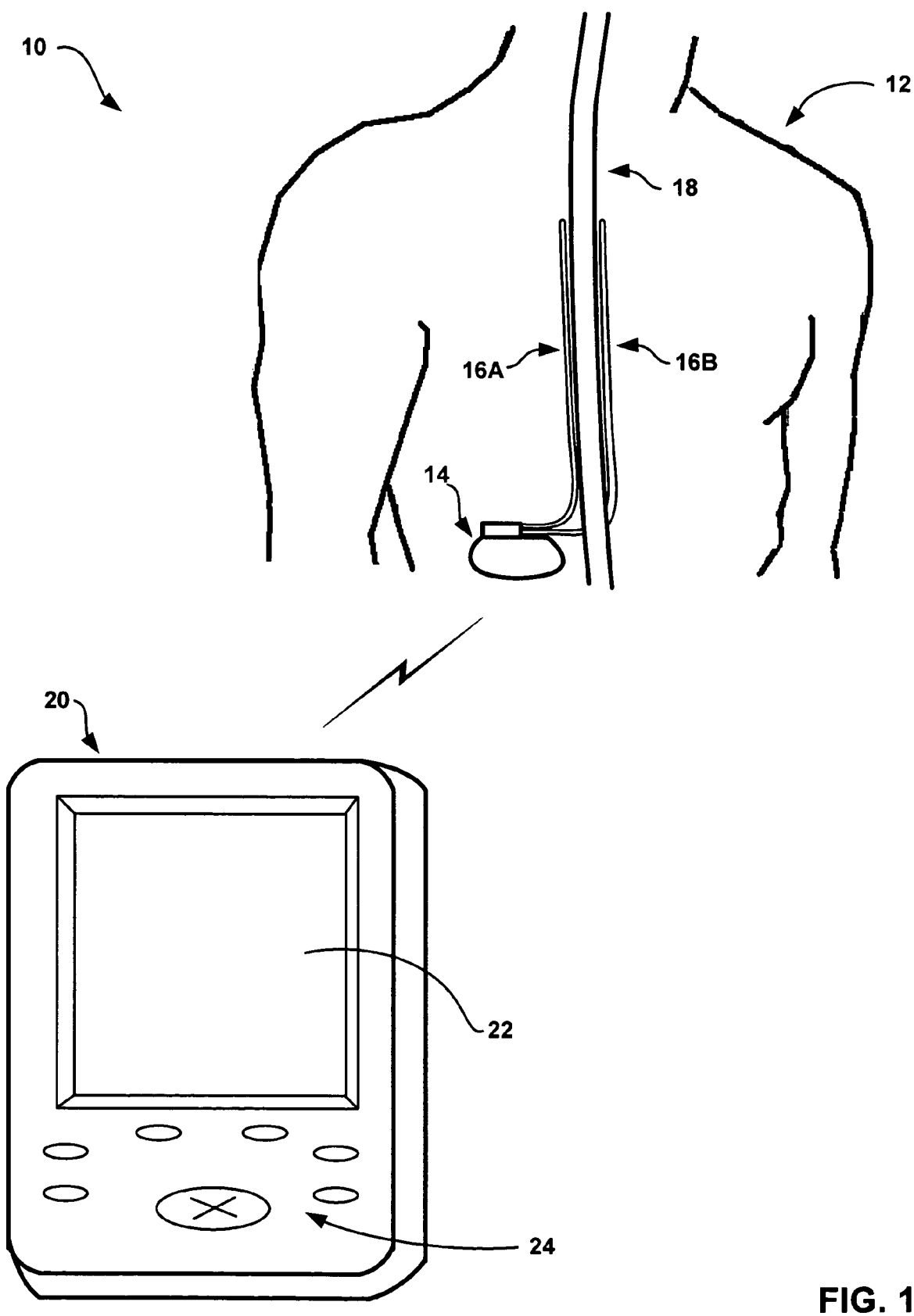
FIG. 1 is a conceptual diagram illustrating an example system for managing delivery of neurostimulation therapy to a patient.

FIG. 1 is a conceptual diagram illustrating an example system 10 for managing delivery of neurostimulation therapy to a patient 12. System 10 includes an implantable medical device 14 that delivers neurostimulation therapy to patient 12. In exemplary embodiments, IMD 14 takes the form of an implantable pulse generator, and delivers neurostimulation therapy to patient 12 in the form of electrical pulses.

IMD 14 delivers neurostimulation therapy to patient 12 via leads 16A and 16B (collectively "leads 16"). Leads 16 may, as shown in FIG. 1, be implanted proximate to the spinal cord 18 of patient 12, and IMD 14 may deliver spinal cord stimulation (SCS) therapy to patient 12 in order to, for example, reduce pain experienced by patient 12. However, the invention is not limited to the configuration of leads 16 shown in FIG. 1, or the delivery of SCS therapy.

IMD 14 may be coupled to any number of leads 16, and the one or more leads 16 may extend from IMD 14 to any position within patient 12 for delivery of neurostimulation to treat any of a number of symptoms or conditions of patient 12. For example, one or more leads 16 may extend from IMD 14 to the brain (not shown) of patient 12, and IMD 14 may deliver deep brain stimulation (DBS) therapy to patient 12 to, for example, treat tremor or epilepsy. As further examples, one or more leads 16 may be implanted proximate to the pelvic nerves (not shown) or stomach (not shown), and IMD 14 may deliver neurostimulation therapy to treat incontinence or gastroparesis.

Each of leads 16 includes one or more electrodes (not shown). The electrodes carried by leads 16 form a set, i.e., array, of electrodes implanted within patient 12. IMD 14 delivers neurostimulation to patient 12 via a selected combination of the electrodes within the electrode set. A combination of electrodes from within an electrode set includes two or more of the electrodes, and includes at least one anode and at least one cathode. A combination of electrodes from within an electrode set may be defined by the polarities, e.g., positive, negative, or off (high impedance), of each of the electrodes within the electrode set.

IMD 14 delivers neurostimulation therapy to patient 12 according to a program. The program may include values for a number of parameters, and the parameter values define the neurostimulation therapy delivered according to that program. In embodiments where IMD 14 delivers neurostimulation therapy in the form of electrical pulses, the parameters may include voltage or current pulse amplitudes, pulse widths, pulse rates, and the like. The program also includes as a parameter information identifying a combination of electrodes from an electrode set implanted within patient 12 that is used by IMD 14 to deliver neurostimulation therapy to patient 12 according to the program. For example, the program may include information indicating the polarities of each of the electrodes of the electrode set for delivery of neurostimulation by IMD 14 according to that program.

System 10 also includes a clinician programmer 20. Clinician programmer 20 may, as shown in FIG. 1, be a handheld computing device. In the illustrated example, clinician programmer 20 includes a display 22, such as a LCD or LED display, to display information to a user, and a keypad 24, which may be used by a user to interact with clinician programmer 20. In some embodiments, display 22 may be a touch screen display, and a user may interact with clinician programmer 20 via display 22. A user may also interact with clinician programmer 20 using peripheral pointing devices, such as a stylus or mouse. Keypad 24 may take the form of an alphanumeric keypad or a reduced set of keys associated with particular functions.

A clinician (not shown) may use clinician programmer 20 to program neurostimulation therapy for patient 12. In general, a clinician programs neurostimulation therapy for patient 12 by specifying one or more programs, e.g., by selecting parameter values for one or more programs, to be used by IMD 14 for delivery of neurostimulation to patient 12. A number of programs, each program including information identifying a combination of electrodes from an electrode set, are tested on patient 12, e.g., clinician programmer 20 directs IMD 14 to deliver neurostimulation therapy to patient 12 according to each program. The clinician selects one or more of the tested programs for use by IMD 14 in delivering neurostimulation therapy to patient 12.

In some embodiments, the clinician enters parameters, directs clinician programmer 20 to program IMD 14 with the parameters, and receives feedback from patient 12 for each program tested on patient 12. In other embodiments, clinician programmer 20 provides an automated testing routine for sequentially testing a number of programs on patient 12. For example, after the clinician initializes clinician programmer 20, patient 12 may interact with clinician programmer 20 to control presentation of, and provide feedback for, a number of automatically generated and sequentially presented programs. Exemplary automated testing routines are described in greater detail in U.S. Pat. No. 6,308,102, issued to Sieracki et al., which is incorporated herein by reference in its entirety.

In any case, the number of possible combinations of electrodes from an electrode set, and consequently the number of possible programs that can be tested on patient 12, can be quite large. As will be described in greater detail below, clinician programmer 20 identifies a subset of the possible combinations of electrodes from electrode set to be tested on patient 12 based on filter information. In some embodiments, clinician programmer 20 presents a listing of the identified subset of electrode combinations to the clinician, so that the clinician may, for example, use the identified electrode combinations as part of programs to test on patient 12. Additionally or alternatively, clinician programmer 20 may automatically present programs that include the identified electrode combinations for testing on patient 12 by sequentially programming IMD 14 to deliver neurostimulation to patient 12 according to the programs, e.g., as a part of an automated testing routine.

By identifying a subset of the possible electrode combinations, clinician programmer 20 avoids testing all possible electrode combinations on patient 12, and may consequently reduce the time required of the clinician and patient 12 to program IMD 14. Further, by automatically identifying the electrode combinations, clinician programmer 20 may allow the clinician to avoid manually entering desired electrode combinations. As will be described in greater detail below, the clinician may provide filter information to clinician programmer 20 that relates to one or more characteristics of desired, e.g., valid, electrode combinations, and clinician programmer 20 may use the filter information to automatically identify the desired electrode combinations for presentation, e.g., within a list or as part of an automated testing routine.

Figure 2:
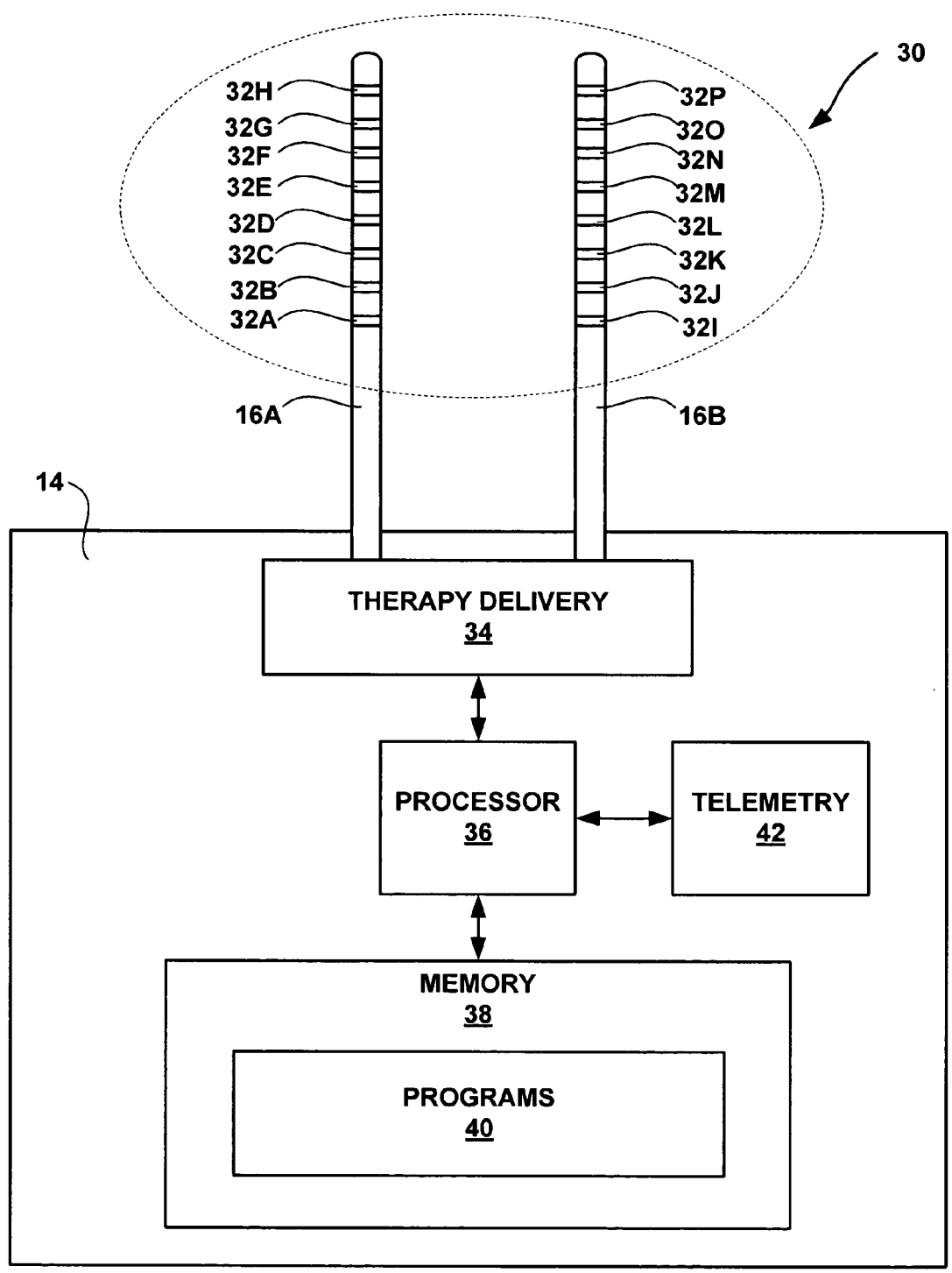
FIG. 2 is a block diagram illustrating an example implantable medical device that delivers neurostimulation therapy to a patient via a combination of electrodes from an electrode set.

FIG. 2 is a block diagram illustrating an example configuration of IMD 14. IMD 14 may deliver neurostimulation therapy via electrodes 32A-H of lead 16A and electrodes 32I-P of lead 16B (collectively "electrodes 32"). Electrodes 32 collectively form a set 30 of electrodes implanted within patient 12 (FIG. 1). Electrodes 32 may be ring electrodes. The configuration, type and number of electrodes 32 within set 30 illustrated in FIG. 2 are merely exemplary.

Electrodes 32 are electrically coupled to a therapy delivery circuit 34 via leads 16. Therapy delivery circuit 34 may, for example, include one or more output pulse generators, e.g., capacitive elements and switches, coupled to a power source such as a battery. Therapy delivery circuit 34 delivers electrical pulses to patient 12 via combination of electrodes 32 from within set 30 that includes two or more active electrodes under the control of a processor 36.

Processor 36 controls therapy delivery circuit 34 to deliver neurostimulation therapy according to a selected program. Specifically, processor 36 may control circuit 34 to deliver electrical pulses with the amplitudes and widths, and at the rates specified by the program. Processor 36 may also control circuit 34 to deliver the pulses via a selected combination of electrodes 32 of set 30, as specified by the program. As indicated above, the program may indicate the polarities, e.g., anode, cathode, or off (high impedance), of each of electrodes 32 within set 30. Processor 36 may include a microprocessor, a controller, a digital signal processor (DSP), an application specific integrated circuit (ASIC), an field programmable gate array (FPGA), discrete logic circuitry, or the like.

IMD 14 also includes a memory 38. In the illustrated embodiment, memory 38 stores one or more programs 40 that are available to be selected by processor 36 for delivery of neurostimulation therapy. Memory 38 may also include program instructions that, when executed by processor 36, cause IMD 14 to perform the functions ascribed to IMD 14 herein. Memory 38 may include any volatile, non-volatile, magnetic, optical, or electrical media, such as a random access memory (RAM), read-only memory (ROM), non-volatile RAM (NVRAM), electrically erasable programmable ROM (EEPROM), flash memory, and the like.

IMD 14 also includes a telemetry circuit 42 that allows processor 36 to communicate with clinician programmer 20. Processor 36 receives programs to test on patient 12 from clinician programmer 20 via telemetry circuit 42 during programming by a clinician. Processor 36 further receives programs 40 selected by the clinician from among the tested programs from clinician programmer 20 via telemetry circuit 42, and stores the received programs 40 within memory 38.

Figure 3:
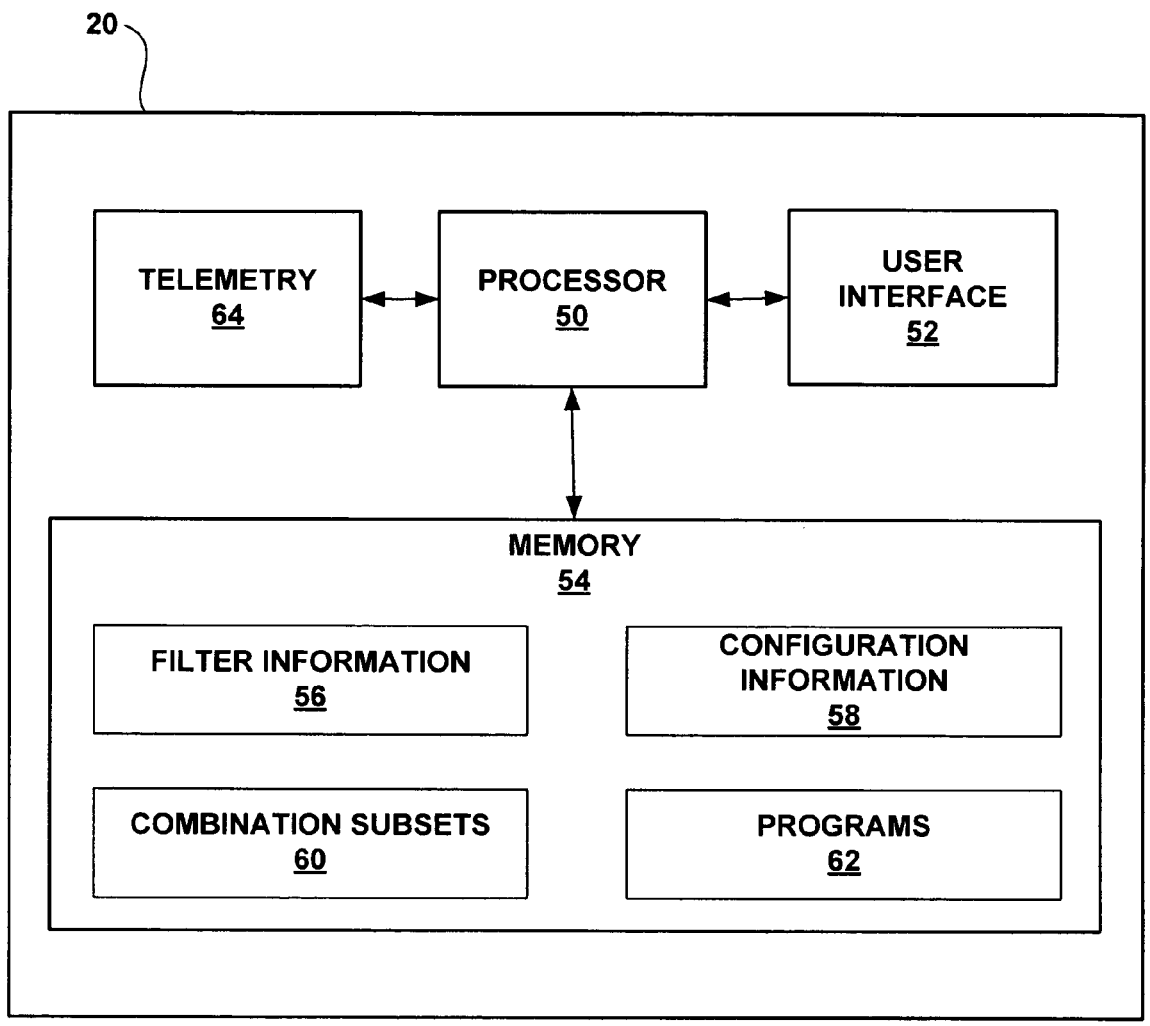
FIG. 3 is a block diagram illustrating an example programming device that identifies combinations of electrodes from an electrode set based on filter information according to the invention.

FIG. 3 is a block diagram illustrating an example configuration of clinician programmer 20. A clinician, and in some cases patient 12, may interact with a processor 50 via a user interface 52 in order to program neurostimulation therapy for patient 12 as described herein. User interface 52 may include display 22 and keypad 24 (FIG. 1), and may also include a touch screen or peripheral pointing devices as described above. Processor 50 may also provide a graphical user interface (GUI) to facilitate interaction with the clinician, as will be described in greater detail below. Processor 50 may include a microprocessor, a controller, a DSP, an ASIC, an FPGA, discrete logic circuitry, or the like.

Clinician programmer 20 also includes a memory 54. In some embodiments, memory 54 includes program instructions that, when executed by processor 50, cause clinician programmer 20 to perform the functions ascribed to clinician programmer 20 herein. Memory 54 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

As illustrated in FIG. 3, memory 54 stores filter information 56. Processor 50 uses filter information 56 to identify a subset of the potential combinations of electrodes 32 within set 30. Specifically processor 50 compares information that describes potential combinations of electrodes 32 from electrode set 30 to filter information 56, and identifies combinations to be included in the subset based on the comparison.

Filter information 56 includes information that relates to at least one characteristic of valid, e.g., desired, electrode combinations. For example, filter information 56 may include information that describes a number of electrodes 32, e.g., two, three, or four electrodes, that valid electrode combinations will include. As another example, filter information 56 may identify a fixed polarity, e.g., anode, cathode, or off, for one or more of electrodes 32 within set 30. Filter information 56 may also include information that describes relational characteristic, e.g., contiguous or guarded cathode, for the active electrodes 32 of a valid combination. In exemplary embodiments, the clinician interacts with processor 50 via the GUI and user interface 52 in order to provide processor 50 with at least a portion of filter information 56.

Memory 54 may also store configuration information 58 that relates to the configuration of electrode set 30. Configuration information 58 may include information describing the number of leads 16 coupled to IMD 14, the number of electrodes 32 per lead 16, the type of leads 16, the position of electrodes 32 on leads 16, and/or the position of electrodes 32 within patient 12. In exemplary embodiments, the clinician interacts with processor 50 via the GUI and user interface 52 in order to provide processor 50 with configuration information 58.

Processor 50 may generate information that describes potential combinations of electrodes 32 to be compared to filter information 56 based on configuration information 58. Specifically, processor 50 may use configuration information 58 that indicates the number of electrodes 32 within set 30 to iteratively generate combinations of the electrodes 32, and may use other configuration information 58 to generate the information that describes the combinations of electrodes 32. Further, processor 50 may determine at least a portion of filter information 56 based on configuration information. For example, processor 50 may use configuration information 58 that indicates the position of electrodes 32 within set 30 to determine that some of electrodes 32 are unsuitable for combination with each other.

Processor 50 compares the information that describes combinations of electrodes 32 to filter information 56 to identify one or more subsets 60 of the potential combinations of electrodes 32 within electrode set 30. Processor 50 may store electrode combination subsets 60 in memory 54. Processor 50 may also present a list of the identified combinations that stored as a subset 60 of combinations to a user, such as the clinician, via user interface 52, e.g., via display 22. The clinician may use the list of combinations to generate programs for testing on patient 12 during programming of IMD 14. In some embodiments, such as embodiments where clinician programmer 20 provides an automated testing routine, processor 50 may incorporate the combinations identified as a subset 60 into programs for sequential testing on patient 12. Such programs may be approved by the clinician before presentation to patient 12.

Whether presented as a list or incorporated into programs, processor 50 may, in some embodiments, randomize the order of combinations within a subset 60. Randomized presentation of electrode combinations may, for example, reduce the possibility that selection of combinations and programs by the clinician for programming of IMD 14 will be biased by the order of presentation or testing. Programs 62 selected by the clinician from among those tested on patient 12 are transmitted to IMD 14 via telemetry circuit 64. The selected programs 62 may also be stored in memory 54, along with the one or more of combination subsets 60, configuration information 56 and filter information 58, as part of a record for patient 12.

A large amount of information may be required to describe each combination of electrodes 32 within an identified subset 60. Consequently, in some embodiments, programmer 20 does not store combination subsets 60 within memory 54 after they are used for testing on patient 12. Instead filter information 56 and configuration information 58 are used as a "compact" description of a combination subset 60, e.g., processor 50 can use filter information 56 and configuration information 58 to reconstruct a combination subset 60 at a later time if necessary. Using filter information 56 and configuration information 58 as a compact description of a combination subset 60 may allow clinician programmer 20 to store records for a greater number of patients 12, and/or may allow for a reduction in the size of clinician programmer 20.

Figure 4:
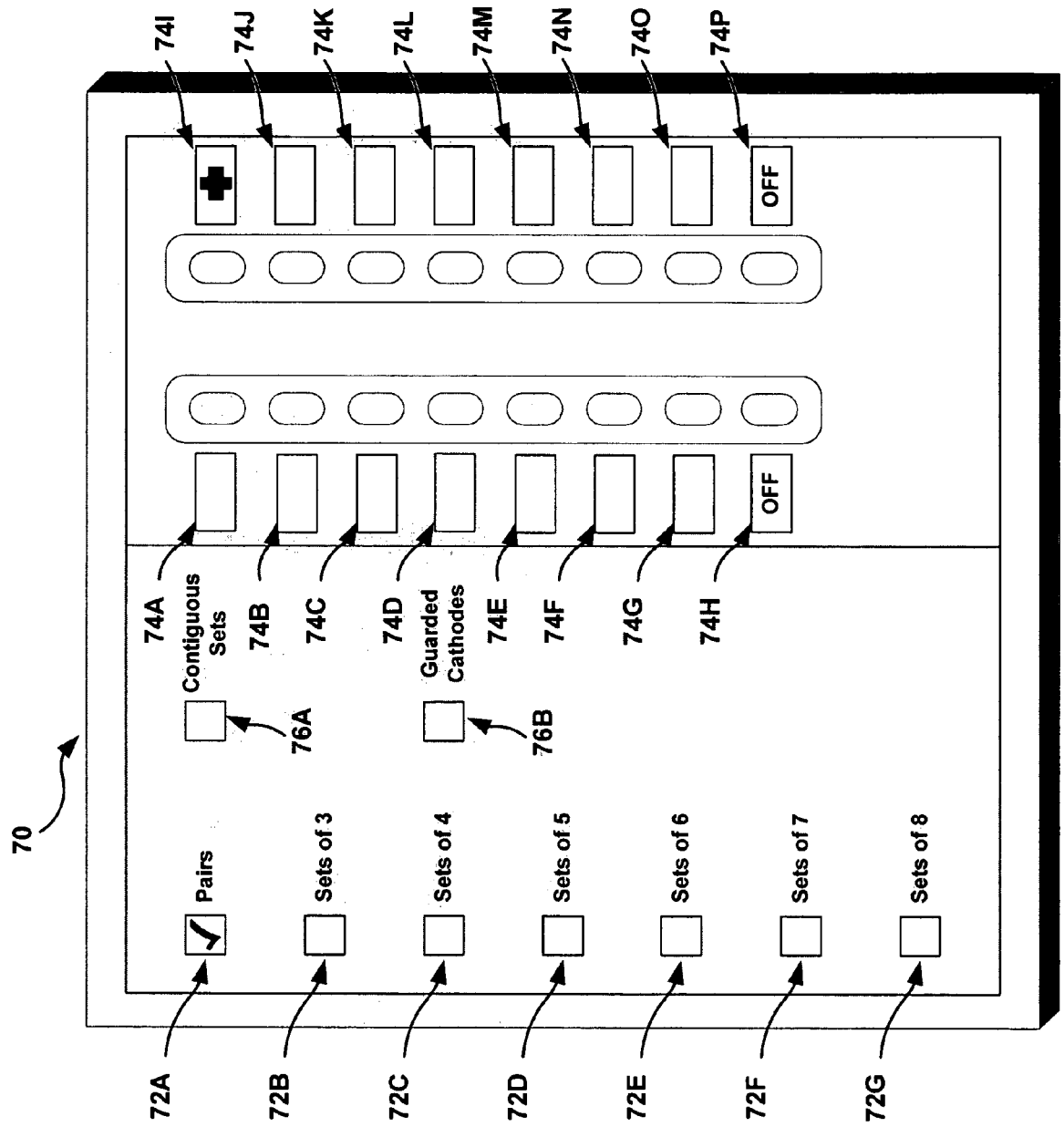
FIG. 4 is a conceptual diagram illustrating an example graphical user interface that may be provided by the programming device of FIG. 3 to allow a user to provide filter information to the device.

FIG. 4 is a conceptual diagram illustrating an example graphical user interface (GUI) 70 that may be provided by clinician programmer 20 to allow a user, e.g., a clinician, to provide filter information 56 to programmer 20. The configuration of GUI 70 illustrated in FIG. 4 is merely exemplary, and is provided for purposes of illustration. Any of a variety of types of fields, e.g., text-boxes, dropdown menus, checkboxes, or the like, arranged in any fashion may be used to collect any of a variety of types of filter information 56.

As discussed above, exemplary filter information 56 includes information indicating a number of electrodes 32 that a valid combination of electrodes 32 must contain for inclusion in a subset 60. As illustrated in FIG. 4, such filter information 56 may be provided to processor 50 by the clinician by clicking one or more of fields 72A-G. Filter information 56 may also include information indicating a fixed polarity for one or more of electrodes 32, which may be entered by toggling the appropriate one or more of fields 74A-P. Each of fields 74 corresponds to one of electrodes 32. The layout of fields 74 within GUI 70 may reflect configuration of electrode set 30, as shown in FIG. 4, and may be determined by processor 50 based on configuration information 58 received from the clinician. In the illustrated example, a configuration of sixteen electrodes 32 carried in groups of eight on each of two leads 16 corresponding to the electrode set illustrated in FIG. 2, the clinician has specified to test only electrode pairs that contain an anode in the upper right contact position, and wherein the lowest electrode positions remain off.

The clinician may also indicate relational characteristics of electrodes 32 within valid combinations as additional filter information 56. For example, the clinician may indicate that only combinations that include contiguous electrodes 32, and/or that include guarded cathode configurations of electrodes 32 are desired. The clinician may indicate such filter information 56 by clicking on one or both of fields 76 of the illustrated example GUI 70.

Figure 5:
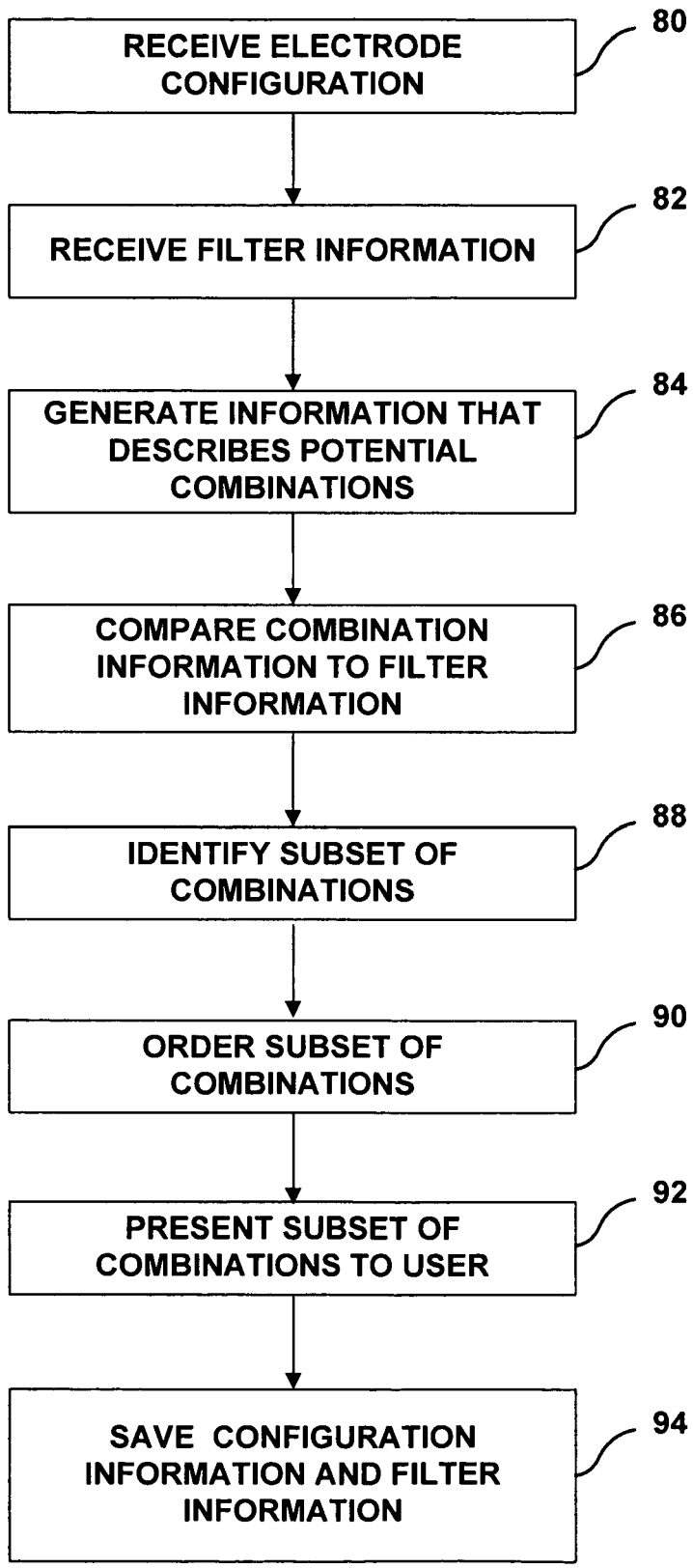
FIG. 5 is a flow diagram illustrating an example method that may be employed by the programming device of FIG. 3 to identify combinations of electrodes from an electrode set based on filter information.

FIG. 5 is a flow chart illustrating an example method that may be employed by clinician programmer 20 to identify combinations of electrodes 32 based on filter information 56. Clinician programmer 20 receives electrode configuration information 58 and filter information 56 from a clinician (80,82). Additional filter information 56 may be generated based on configuration information 58. For example, processor 50 may identify electrodes 32 that cannot be combined with each other due to the configuration of electrode set 30 as indicated by configuration information 58.

Processor 50 generates information that describes each of a number of possible combinations of the electrodes 32 within electrode set 30 based on the configuration information 58 (84), and compares the generated information to filter information 56 (86). Processor 50 identifies a subset 60 of the possible combinations of electrodes 32 based on comparison (88), e.g., identifies combinations of electrodes 32 that meet the requirements indicated by the clinician and inherent in the configuration of electrode set 30.

In some embodiments, processor 50 orders the identified electrode combinations in a order that is different from the order that resulted from the generation and comparison process (90) for presentation to a user (92). For example, the order may be random. Processor 50 may present a listing of the subset 60 of electrode combinations to a clinician via user interface 52, and/or may automatically generate programs that include the electrode combinations within the subset 90 and sequentially direct IMD 14 to deliver neurostimulation according to the programs for testing of the electrode combinations on patient 12, as described above. In order to reduce the size of a record for patient 12, the configuration information 58 and filter information 56 may be stored in memory 54 of the clinician programmer 20 as a compact description of the tested subset 60 of electrode combinations (94).

Figure 6:
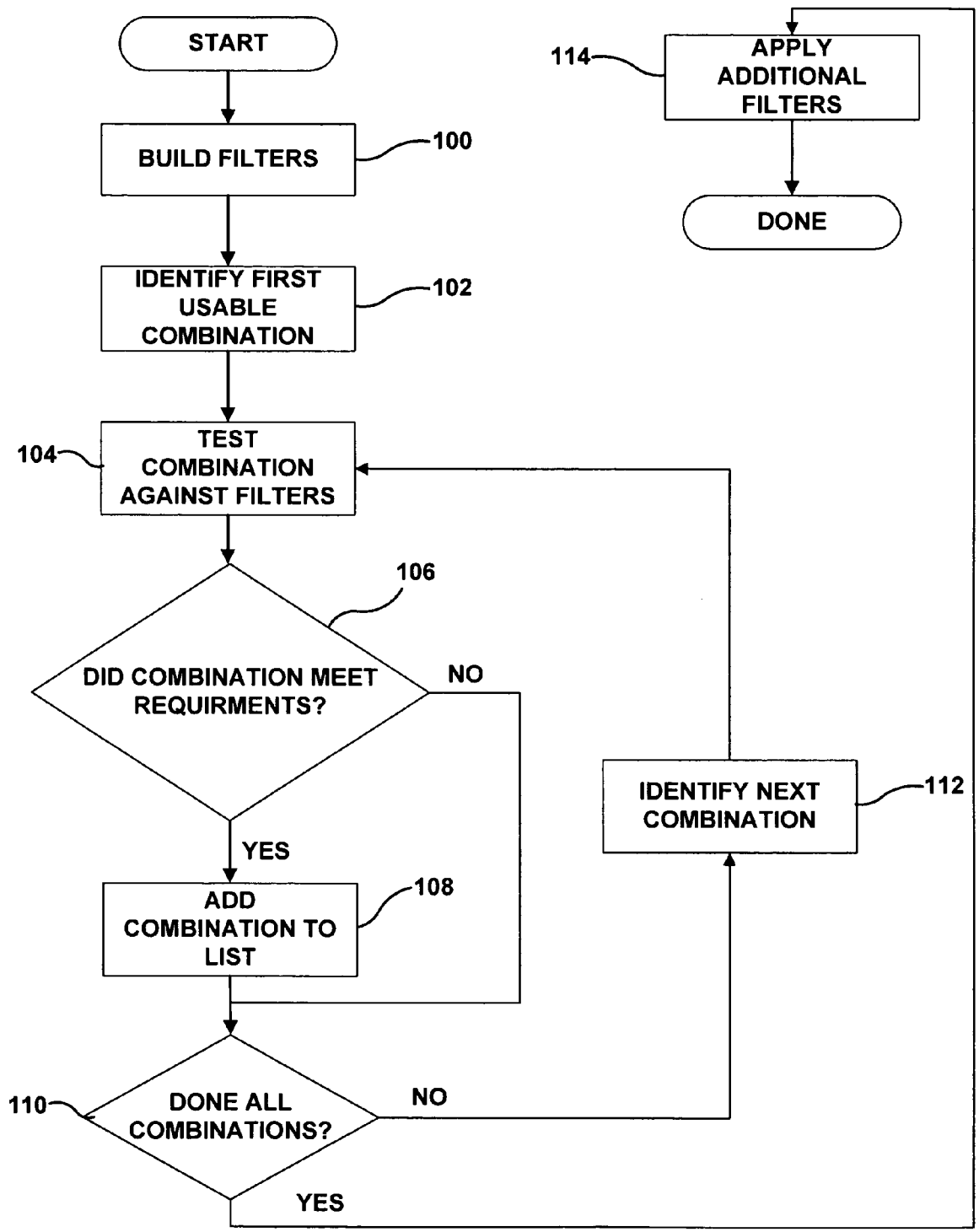
FIG. 6 is a flow diagram illustrating another example method that may be employed by the programming device of FIG. 3 to identify combinations of electrodes from an electrode set based on filter information.

FIG. 6 is a flowchart illustrating another example method that may be employed by clinician programmer 20 to identify combinations of electrodes 32 based on filter information 58. In particular, FIG. 6 illustrates an iterative method that may be employed by clinician programmer 20 to generate information that describes combinations of electrodes for comparison to filter information 56.

Processor 50 builds filters according to filter information 56 received via user interface 52 and determined based on configuration information 58 (100), and generates information that identifies a first combination of electrodes 32 within electrode set 30 (102). In some embodiments, memory 54 stores information that associates electrode configurations 58 and filter information 56 with a first valid electrode combination. By retrieving a previously identified first valid combination, processor 50 may avoid testing unusable combinations of electrodes 32, and may consequently reduce the total amount of iterations, and therefore time, required to compare each potential combination of electrodes 32 to the filters.

The first combination is compared to the filters (104). If a first valid combination is pre-identified, the next combination is identified via iteration, e.g., an electrode combination with the polarity of one or more electrodes toggled from that of the first valid combination, and the next combination is compared to the filters. The processor 50 determines whether the combination meets the filter requirements (106). If the combination meets the filter requirements, processor 50 adds the combination to subset 90 (108).

If processor 50 has not compared each possible combination of electrodes 32 from set 30 to the filters (110), processor 50 identifies the next combination to test (112). Processor 50 may identify the next combination to test as, for example, an electrode combination with the polarity of one of the active electrodes toggled from the previously tested electrode combination, with the position of one of the active electrodes moved from the previously tested electrode combination, or with an active electrode in addition to those of the previously tested electrode combination. When all the possible combinations of electrodes 32 within set 30 have been tested, or when a user otherwise ends the iterative comparison processes, additional filters may be applied to the subset 90 (114). For example, a filter limiting the total number of electrode combinations within a subset 90 may be applied to further reduce the size of subset 90. If application of filter information 56 leads to identification of no valid combinations of electrodes, clinician programmer 20 may alert the user so that the user can amend filter information 56 or take other appropriate action.

Various embodiments of the invention have been described. However, one skilled in the art will appreciate that various modifications may be made to these embodiments without departing from the scope of the invention. For example, comparison of combinations of electrodes to filter information need not be in any particular sequential order or even sequential at all. Filter information may include a plurality of filters, and each of the plurality of filters may be iteratively applied to the potential combinations of electrodes, e.g., potential states of the electrode set, either simultaneously or sequentially. Moreover, where multiple filters are applied sequentially, they may be applied in any order.

For example, in some embodiments, a first filter is constructed based on filter information provided by the user. Such a filter may be applied during a first sequencing through potential combinations of electrodes of the set to, for example, identify combinations where one particular electrode is an anode. A second filter may be constructed based on the inherent limitations on electrode combinations to, for example, identify whether combinations include at least one anode and cathode. A third filter may be constructed based on physical limitations on electrode combinations, e.g., configuration information, to identify whether electrodes are spatially suited for combination. The second and third filters may be applied to each potential combination of electrodes from within the set during separate second and third iterations through potential combinations, or simultaneously with the first filter during the first sequencing through potential combinations.

Further, although programs are described herein as stored in IMD 14, the invention is not so limited. In some embodiments, system 10 includes a patient programmer that patient 12 may use to control delivery of therapy by IMD 14. Patient 12 may activate or adjust delivery of therapy by IMD 14, and may select from among a plurality of programs used by IMD 14 to deliver neurostimulation therapy via the patient programmer. In some embodiments, the patient programmer stores the programs used by IMD 14, and transmits a selected program to IMD 14 via device telemetry. In some embodiments, system 10 is a radio-frequency (RF) neurostimulation system, wherein IMD 14 receives both programs and operating power from the patient programmer.

Additionally, although described herein in the context of implantable medical device and implanted electrode sets, the invention is not so limited. For example, an electrode set may be external to a patient, e.g., the electrodes may be placed on the skin of the patient, and used to deliver transcutaneous electrical nerve stimulation (TENS) to the patient. These and other embodiments are within the scope of the following claims.

The invention claimed is:

1. A method comprising:
comparing information that identifies combinations of electrodes from within a set of electrodes to filter information that relates to at least one characteristic of valid combinations of electrodes; and
identifying a subset of the combinations of electrodes based on the comparison, the subset comprising a plurality of the combinations of electrodes, wherein the subset includes only valid combinations of electrodes.

2. The method of claim 1, further comprising receiving at least some of the filter information from a user.

3. The method of claim 1, further comprising:
receiving information describing a configuration of the set of electrodes from a user; and
determining at least some of the filter information based on the configuration.

4. The method of claim 1, wherein the at least one characteristic identifies a number of electrodes for valid electrode combinations.

5. The method of claim 1, wherein the at least one characteristic identifies a fixed polarity of one of the electrodes of the electrode set for valid electrode combinations.

6. The method of claim 1, wherein the at least one characteristic identifies a relational characteristic of electrodes within a valid combination of electrodes.

7. The method of claim 1, further comprising presenting a list of the combinations of electrodes within the subset to a user.

8. The method of claim 1, further comprising sequentially configuring the electrodes within the set of electrodes according to the combinations of electrodes within the subset for testing of the combinations of electrodes within the subset on a patient.

9. The method of claim 1, further comprising storing the filter information as a description of the subset of combinations of electrodes.

10. The method of claim 1, wherein the set of electrodes is implanted within a patient.

11. A computer-readable medium comprising instructions that cause a programmable processor to:
compare information that identifies combinations of electrodes from within a set of electrodes to filter information that relates to at least one characteristic of valid combinations of electrodes; and
identify a subset of the combinations of electrodes based on the comparison, the subset comprising a plurality of the combinations of electrodes, wherein the subset includes only valid combinations of electrodes.

12. The computer-readable medium of claim 11, further comprising instructions that cause a programmable processor to receive at least some of the filter information from a user.

13. The computer-readable medium of claim 11, further comprising instructions that cause a programmable processor to:
receive information describing a configuration of the set of electrodes from a user; and
determine at least some of the filter information based on the configuration.

14. The computer-readable medium of claim 11, wherein the at least one characteristic identifies a number of electrodes for valid electrode combinations.

15. The computer-readable medium of claim 11, wherein the at least one characteristic identifies a fixed polarity of one of the electrodes of the electrode set for valid electrode combinations.

16. The computer-readable medium of claim 11, wherein the at least one characteristic identifies a relational characteristic of electrodes within a valid combination of electrodes.

17. The computer-readable medium of claim 11, further comprising instructions that cause a programmable processor to present a list of the combinations of electrodes within the subset to a user.

18. The computer-readable medium of claim 11, further comprising instructions that cause a programmable processor to sequentially configure the electrodes within the set of electrodes according to the combinations of electrodes within the subset for testing of the combinations of electrodes within the subset on a patient.

19. The computer-readable medium of claim 11, further comprising instructions that cause a programmable processor to store the filter information as a description of the subset of combinations of electrodes.

20. The computer-readable medium of claim 11, wherein the set of electrodes in implanted within a patient.

21. A device comprising:
a user interface; and
a processor to compare information that identifies combinations of electrodes from within a set of electrodes to filter information that relates to at least one characteristic of valid combinations of electrodes, and identify a subset of the combinations of electrodes based on the comparison, the subset comprising a plurality of the combinations of electrodes, wherein the processor receives at least some of the filter information from a user via the user interface, and wherein the subset includes only valid combinations of electrodes.

22. The device of claim 21, wherein the at least one characteristic identifies a number of electrodes for valid electrode combinations.

23. The device of claim 21, wherein the at least one characteristic identifies a fixed polarity of one of the electrodes of the electrode set for valid electrode combinations.

24. The device of claim 21, wherein the at least one characteristic identifies a relational characteristic of electrodes within a valid combination of electrodes.

25. The device of claim 21, wherein the processor presents a list of the combinations of electrodes within the subset to the user via the user interface.

26. The device of claim 21, further comprising a memory to store the filter information as a description of the subset of combinations of electrodes.

27. The device of claim 21, wherein the device comprises a programming device.

28. The device of claim 21, wherein the device comprises a handheld computer.

29. The device of claim 21, wherein the set of electrodes is implanted within a patient.

30. The method of claim 1, wherein the at least one characteristic of valid electrode configurations comprises a guarded electrode configuration.

* * * * *

UNITED STATES PATENT AND TRADEMARK OFFICE
CERTIFICATE OF CORRECTION

| | | |
|---|---|---|
| PATENT NO. | : 7,603,177 B2 | Page 1 of 1 |
| APPLICATION NO. | : 11/413626 | |
| DATED | : October 13, 2009 | |
| INVENTOR(S) | : Sieracki et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 693 days.

Signed and Sealed this

Fifth Day of October, 2010

David J. Kappos
*Director of the United States Patent and Trademark Office*